(12) United States Patent
Ali et al.

(10) Patent No.: US 11,759,322 B1
(45) Date of Patent: Sep. 19, 2023

(54) METHOD OF TREATING OSTEOARTHRITIS OF THE KNEE

(71) Applicants: Sadat A. Ali, Alkhobar (SA); Hussain Khalil Alomar, Alkhobar (SA); Omar Saleem A. Dahduli, Alkhobar (SA)

(72) Inventors: Sadat A. Ali, Alkhobar (SA); Hussain Khalil Alomar, Alkhobar (SA); Omar Saleem A. Dahduli, Alkhobar (SA)

( * ) Notice: Subject to any disclaimer, the term of this patent is extended or adjusted under 35 U.S.C. 154(b) by 0 days.

(21) Appl. No.: 17/971,463

(22) Filed: Oct. 21, 2022

(51) Int. Cl.
| | | |
|---|---|---|
| *A61F 2/38* | (2006.01) | |
| *A61F 2/36* | (2006.01) | |
| *A61F 2/30* | (2006.01) | |
| *A61L 27/36* | (2006.01) | |
| *A61B 17/86* | (2006.01) | |

(52) U.S. Cl.
CPC ...... *A61F 2/30756* (2013.01); *A61L 27/3654* (2013.01); *A61B 17/864* (2013.01); *A61B 17/8645* (2013.01)

(58) Field of Classification Search
CPC .. A61F 2/30756; A61F 2/3603; A61F 2/3859; A61F 2/389
See application file for complete search history.

(56) References Cited

U.S. PATENT DOCUMENTS

| | | | |
|---|---|---|---|
| 5,919,196 | A | 7/1999 | Bobic et al. |
| 6,591,581 | B2 | 7/2003 | Schmieding |
| 6,592,588 | B1 | 7/2003 | Bobic et al. |
| 2017/0215894 | A1 | 8/2017 | Karnes et al. |

FOREIGN PATENT DOCUMENTS

KR  10-1662954 B1  10/2016

OTHER PUBLICATIONS

Haber et al., "Osteochondral Allograft Transplantation for the Knee: Post-Operative Rehabilitation," The International Journal of Sports Physical Therapy, vol. 14, No. 3, Jun. 2019, p. 487.
"Cartilage Transplant Cartilage cell transplant for osteoarthritis of the knee," © 2000-2022 MVZ Gelenk-Klinik, Sep. 29, 2020.

*Primary Examiner* — Jason-Dennis N Stewart
(74) *Attorney, Agent, or Firm* — Nath, Goldberg & Meyer; Richard C. Litman

(57) ABSTRACT

The method of treating osteoarthritis of the knee includes replacing the entire cartilage of the femoral condyle, proximal tibia, and two menisci using allograft, while retaining the native cruciate ligaments. The method includes resection of the proximal tibia and the femoral condyle. A first allograft is configured to replace the femoral condyle and includes whole cartilage with about 5 mm to about 7 mm of cancellous bone attached. The first allograft can have a slot or opening through which native cruciate ligaments may pass. A second allograft can replace the upper end of the tibia and menisci. The second allograft can include a slot or opening through which native cruciate ligaments may pass. The first and second allografts can be fixed using cancellous screws. The procedure can provide patients with full knee flexion, and thereby enable kneeling, e.g., as required in the Islamic prayers, full kneeling, or any other activity which requires full flexion of the knee and kneeling.

10 Claims, 2 Drawing Sheets

METHOD OF TREATING OSTEOARTHRITIS OF THE KNEE

BACKGROUND

1. Field

The disclosure of the present patent application relates to a method of treating osteoarthritis of the knee, and particularly to a method of treating osteoarthritis of the knee by replacing cartilage in the femur and tibia with allograft.

2. Description of the Related Art

Knee Osteoarthritis (OA) is the most common, degenerative type of arthritis, and occurs most often in people fifty years of age and older. In osteoarthritis, the cartilage in the knee joint gradually wears away. The incidence of knee OA was 203 per 10,000 persons per year. Correspondingly, there are around annual 86.7 (95% CI, 45.3-141.3) million individuals with incident knee OA in 2020 worldwide.

The four stages of osteoarthritis are: Stage 1 (minor)—associated with minor wear-and-tear in the joints and little to no pain in the affected area; Stage 2 (mild)—associated with more noticeable bone spurs; Stage 3 (moderate)—associated with beginning of erosion of cartilage in the affected area; and Stage 4 (severe)—associated with significant pain.

Management of OA includes weight loss, exercise, pain relievers, anti-inflammatory drugs, injections of corticosteroids or hyaluronic acid into the knee, and alternative therapies using devices (such as braces), physical and occupational therapy, and surgery.

Surgery is reserved for patients whose symptoms have not responded to other treatments. The well-accepted indication for surgery is continued pain and disability despite conservative treatment. The most effective surgical intervention is total knee replacement (TKA), with excellent patient outcomes following total joint replacement of the knee. The complications of TKA are many, including amputations, neurovascular, vascular injury and bleeding, peroneal nerve injury, extensor mechanism, patellar prosthesis loosening, patellar clunk, patellar maltracking, extensor mechanism rupture, periprosthetic infection, periprosthetic fracture, metal hypersensitivity, wound complications, instability (tibio-femoral), stiffness, and infection ending in amputation.

Thus, a method for treating osteoarthritis solving the aforementioned problems is desired.

SUMMARY

The method of treating osteoarthritis of the knee includes replacing the entire cartilage of the femoral condyle, proximal tibia, and two menisci with allograft, while retaining the native cruciate ligaments. The method includes resection of the proximal tibia and the femoral condyle. A first allograft is configured to replace the femoral condyle and includes whole cartilage with about 5 mm to about 9 mm of cancellous bone attached. The first allograft can have a slot or opening through which native cruciate ligaments may pass. A second allograft can replace the upper end of the tibia and menisci. The second allograft can include a slot or opening through which native cruciate ligaments may pass. The first and second allografts can be fixed using cancellous screws. For example, one cancellous screw can be positioned on each side of the allograft. The procedure can provide patients with full knee flexion and, thereby, enable kneeling, e.g., as required in the Islamic prayer.

Both the tibial and femur allograft surfaces can carry a minimum of 5 mm of cancellous bone. This can help to initiate early union and incorporation to the native bone. The two screws, e.g., two 6.5 mm cancellous screws, one on each side of each allograft can facilitate sufficient fixation to the femur and tibia.

These and other features of the present subject matter will become readily apparent upon further review of the following specification and drawings.

BRIEF DESCRIPTION OF THE DRAWINGS

FIG. 4 is a perspective view of the tibial allograft with 10 mm thickness of cancellous bone and openings for native ACL and PCL to pass through.

Similar reference characters denote corresponding features consistently throughout the attached drawings.

DETAILED DESCRIPTION OF THE PREFERRED EMBODIMENTS

The method of treating osteoarthritis of the knee includes resection of the proximal tibia and the femoral condyle and cancellous bone grafting after resection. The cancellous bone grafting includes replacing the femoral condyle with a first allograft and the upper end of the tibia and menisci with a second allograft. The first and second allografts are secured in position using cancellous screws. For example, one cancellous screw can be positioned on each side of each allograft. In an embodiment, each cancellous screw may be a 6.5 mm cannulated, cancellous, headless screw. The procedure can provide patients with full knee flexion, and thereby enable kneeling, e.g., as required in the Islamic prayer.

Figure 1:
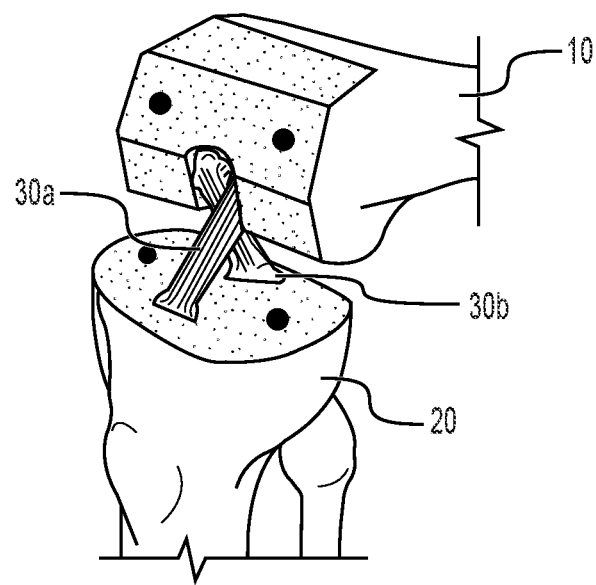
FIG. 1 is a perspective view of the femur and tibia after resection with native anterior and posterior cruciate ligaments intact.
Figure 2:
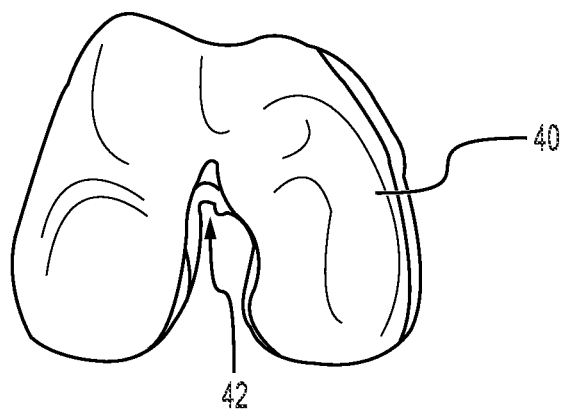
FIG. 2 is a frontal view of a femoral cartilage allograft, which includes cartilage and cancellous bone.
Figure 3:
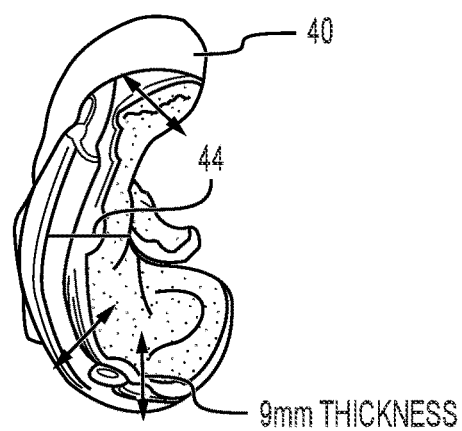
FIG. 3 is a sagittal section view of the femoral cartilage allograft of FIG. 2.
Figure 4:
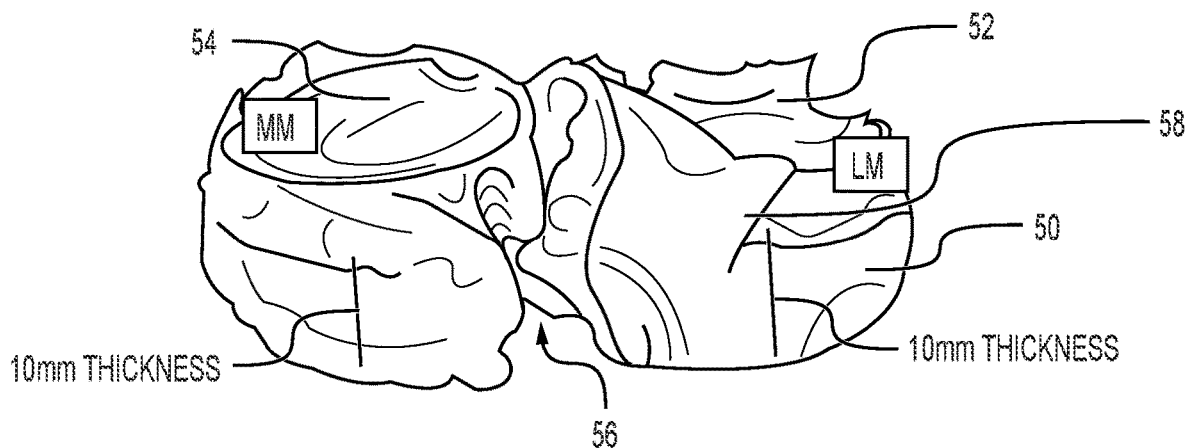
Figure 5:
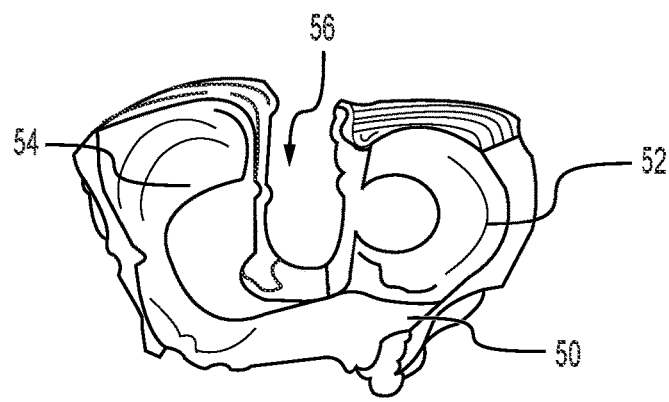
FIG. 5 is a top view of the tibial allograft with cancellous bone showing the two menisci.

In an embodiment, the resection incudes resection of the entire cartilage of the femoral condyle from the femur 10 and resection of the entire proximal tibia and two menisci from the tibia 20 such that the native cruciate ligaments are retained 30a, 30b (FIG. 1). Both the tibial and femur allograft surfaces can carry a minimum of 5 mm of cancellous bone. This can help to initiate early union and incorporation with the native bone. The cancellous screws affixed to each allograft can facilitate sufficient fixation of the allografts to the femur and tibia. The first allograft 40 (the femoral allograft) can have a slot or opening 42 through which the retained, native cruciate ligaments 30a, 30b may pass (FIG. 2). The first allograft 40 can have about 9 mm of cancellous bone attached (FIG. 3). For the tibia, the second allograft 58 is configured to replace the upper end of the tibia and menisci and includes an opening 56 for passage of the native cruciate ligaments (FIG. 4). The second allograft (the tibial allograft) can include cartilage and cancellous bone 50. The thickness of the cancellous bone of the second allograft 58 can be about 10 mm (FIG. 4). The slot or opening 56 can extend through the second allograft 58, through which the retained, native cruciate ligaments 30a, 30b may pass.

Resection can include making a medial parapatellar incision. Three essential landmarks for the incision include the proximal medial border of the quadriceps tendon, a point halfway between the vastus *medialis* insertion and the medial edge of the tibial tubercle. The patella can be everted laterally prior to standard dissection. The patellar tendon can be divided with about 3 mm to about 4 mm of the tendon attached to the medial border of the patella. This can further mobilize the patella and improve the exposure to the lateral compartment. Care must be taken to avoid inadvertently injuring the quadriceps tendon, the popliteus tendon, or lateral collateral ligament. During the procedure, complete removal of the synovium should be avoided as the synovium can be a source of lubrication for the replaced cartilage. As articular cartilage does not contain blood vessels, the continued survival of the cartilage depends on the lubrication of the joint.

Preferably, the tibia is prepared first. When the proximal tibial resection is being performed, the medial collateral ligament (MCL) can be protected during the resection by placement of a metallic retractor between the ligament and the medial border of the proximal tibia. Since the native cruciates are retained, the desired tibial cuts can be performed using a slotted osteotome or a sleeved oscillating saw. Then, a 1 cm wide osteotome can be inserted into the slot to protect the posterior tissues from excursion of the oscillating saw. Alternatively, the tibial spine in front of the ligament can be shaped, e.g., wedge-shaped, with an oscillating saw or reciprocating saw.

The allografts are preferably pre-designed. The sizing of the allograft can be made based on computerized tomography and exact cuts can be made on the allograft based on the size of the patient's knee joint. For the tibia, the allografts can be configured to replace the upper end of the tibia and menisci and include openings for passage of the native cruciate ligaments. The tibial component can be 15 mm of the proximal tibia.

Allograft harvesting can be done according to the criteria of the American Association of Tissue Banks, in sterile conditions followed by irradiating the tissue at 25,000 Gy and stored at −70° C. The sizing of the allograft can be based on the computerized tomography.

The allograft can be checked for sizing prior to transplant. For the tibia, the junction between the medial and central thirds of the tubercle can be used as a landmark. A determined thickness of the tibial tubercle can be equivalent to the thinnest portion of the composite, unless it is obvious that flexion and extension spaces will require a thicker size. Once the correct thickness is achieved, excess bone can be removed from the allograft using a saw. Once the size and thickness of the tibial allograft is decided, the allograft can be held using K wires under the medial and lateral meniscus. The screws can connect the allograft to the shaft of the tibia.

In preparing the femur, the anatomy of the intercondylar notch should be checked. The anterior cruciate ligament (ACL) and posterior cruciate ligament (PCL) origin should be exposed and defined. The medullary canal of the femur can be entered approximately 1 cm above the origin of the PCL and a few millimeters medial to the true center of the intercondylar notch. One way to define this is to draw a Whiteside line down the deepest part of the trochlear sulcus and mark the entry point 1 cm above the top of the intercondylar notch and several mm medial to the Whiteside line. This can be done by passing a line down the center of the shaft of the femur and seeing where it exits in the intercondylar notch. Standard cuts of the femur can be made as in a routine implant-driven total knee replacement.

The femur allograft can be sized based on the computerized tomography scan of the knee of the patient and can be custom built. For the final preparation of the femur, the allograft can be placed on the femur condyle and manually pushed to the cancellous bone on the femur. The allograft can then be properly positioned in the medial-lateral dimension and fixed with two cancellous screws on the non-weight bearing sites of the condyles.

The intra-operative criterion for cementless fixation combines the assessment of the precision of the fit as viewed from the side and the force required to disimpact the trial from the femoral bone. The disimpaction test is admittedly crude, but appears to be effective in screening patients. If the trial femoral component can be removed by hand or with a very light tap of the slap hammer of the insertion/extraction device, the femoral component always is cemented. If it takes multiple taps of the slap hammer and trial extraction is difficult, cementless fixation is appropriate. In borderline cases, the femur should be cemented. The precision of the cuts as viewed from the side does not appear to be as critical to the success of cementless fixation.

Post operatively, antibiotics can be administered to the patient for a week and anti-thromotic medication for 4 weeks. Rehabilitation protocols continue to evolve and accelerate. Patients begin ambulation the day of surgery, with partial weight bearing. A knee immobilizer can be applied at night to maintain extension and provide comfort for transfers and initial ambulation the day of surgery. Weight-bearing for distances is protected with crutches or a walker for 6 weeks. All support is discontinued at 12 weeks, except for a cane for distances at the patient's discretion.

The initial post-operative visit can occur approximately 4 weeks after surgery. Sutures can be removed at 14 days after surgery. The wound can then be checked, along with range of motion and ambulatory ability. Postoperative radiographs including a standing AP, lateral, and skyline view can be obtained. If post-operative range of motion is less than expected, a knee manipulation can be performed 6-8 weeks after surgery.

It is to be understood that the method for treating osteoarthritis of the knee is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of treating osteoarthritis of the knee of a patient in need thereof, the patient's knee including a proximal tibia and medial and lateral femoral condyles, comprising the steps of:
   resecting the proximal tibia and the femoral condyles of the patient while retaining native cruciate ligaments;
   replacing all cartilage from the proximal tibia and menisci between the proximal tibia and the femoral condyles using a first allograft of cartilage having attached cancellous bone; and
   replacing all cartilage from the femoral condyle with a second allograft of cartilage having attached cancellous bone, the first and second allografts having openings defined therein through which the native cruciate ligaments may pass.

2. The method of treating osteoarthritis of the knee according to claim 1, wherein the first allograft is affixed to the tibia using first and second cancellous screws.

3. The method according to claim 1, wherein the second allograft is affixed to the femur using third and fourth cancellous screws.

4. The method according to claim 1, wherein the first, second, third, and fourth cancellous screws are 6.5 mm cannulated, cancellous, headless screws.

5. The method according to claim 1, wherein the tibia has an upper end and the step of resecting the proximal tibia includes resecting all cartilage from the proximal tibia and resecting the menisci.

6. The method of claim 1, wherein the first and second allografts have a surface carrying cancellous bone.

7. The method of claim 6, wherein the first and second allograft surfaces each carry 5 mm of cancellous bone.

8. The method of claim 1, wherein the first allograft has a thickness of about 10 mm.

9. The method of claim 1, wherein the second allograft has a thickness of about 9 mm.

10. The method of claim 1, wherein at least a portion of the synovium is retained during the resecting step.

\* \* \* \* \*